United States Patent [19]
Young

[11] Patent Number: 5,997,493
[45] Date of Patent: Dec. 7, 1999

[54] "HINGE WITH MOVEMENT LIMITATION"

[75] Inventor: David Ernest Young, Watlington, United Kingdom

[73] Assignee: Johnson & JohnsonProfessional, Inc., Raynham, Mass.

[21] Appl. No.: 08/931,677

[22] Filed: Sep. 16, 1997

[51] Int. Cl.[6] .................................................. A61F 5/00
[52] U.S. Cl. ................................ 602/16; 602/5; 602/16; 602/20; 602/23; 602/26
[58] Field of Search .................................. 602/5, 16, 23, 602/26, 20

[56] References Cited

U.S. PATENT DOCUMENTS

| | | | |
|---|---|---|---|
| 4,817,588 | 4/1989 | Bledsoe | 602/16 |
| 4,982,732 | 1/1991 | Morris | 602/16 |
| 5,000,169 | 3/1991 | Swicegood et al. | 602/26 X |
| 5,460,599 | 10/1995 | Davis et al. | 602/16 X |
| 5,672,152 | 9/1997 | Mason et al. | 602/26 |
| 5,814,000 | 9/1998 | Kilbey | 602/16 |

Primary Examiner—Richard J. Apley
Assistant Examiner—Jayne Saydah
Attorney, Agent, or Firm—Michael Q. Tatlow

[57] ABSTRACT

A uniaxial orthopaedic hinge (1000, 2000) has a substantially circular body forming a recessed housing (1022, 2022). The upper surface of the housing (1022, 2022) is furnished with a concentric arcuate circular slot (1038, 2038) disposed inwardly from the periphery. The inner surface (2040) is provided with equally spaced radial teeth (1044, 2044). A back plate (1006, 2006) has an extension into a stub arm (1004, 2004) for attaching to the arm of an orthosis and is fixed to the recessed housing (1022, 2022). A locking plate (1008, 2008) also has an extension into a stub arm (1002, 2002) and is disposed in a parallel manner between the recessed housing (1022, 2022) and the back plate (1006, 2006). Adjustable locking means are in the form of quadrants (1050, 1052, 2050, 2052) each having a pusher (1066, 1068, 2066, 2068) which extends through the arcuate slot (1038, 2038) in the recessed housing (1022, 2022) and toothed locking faces (1042, 2042) on either side of a base portion (1054, 1056, 2054, 2056), the teeth being adapted so as to engage with those on the inner aspect (2040) of the recessed housing (1022, 2022). The quadrants (1050, 1052, 2050, 2052) are each provided with a compression spring (1074, 1076, 2074, 2068) in the base which sustains the engaged condition until the pusher (1066, 1068, 2066, 2068) is depressed after which the quadrants (1050, 1052, 2050, 2052) may be moved along the slot (1038, 2038) to a new position. The locking plate (1008, 2008) is provided with an flange abutment stop (1088, 2088) disposed in such a manner that it always lies under the slot (1038, 2038) in the hinge body and adapted to co-operate with the quadrants (1050, 1052, 2050, 2052) so that the hinge (1000, 2000) may be locked in a selected position or allowed any desired range of angular motion which is a multiple of the angular increments of the hinge teeth angle.

4 Claims, 6 Drawing Sheets

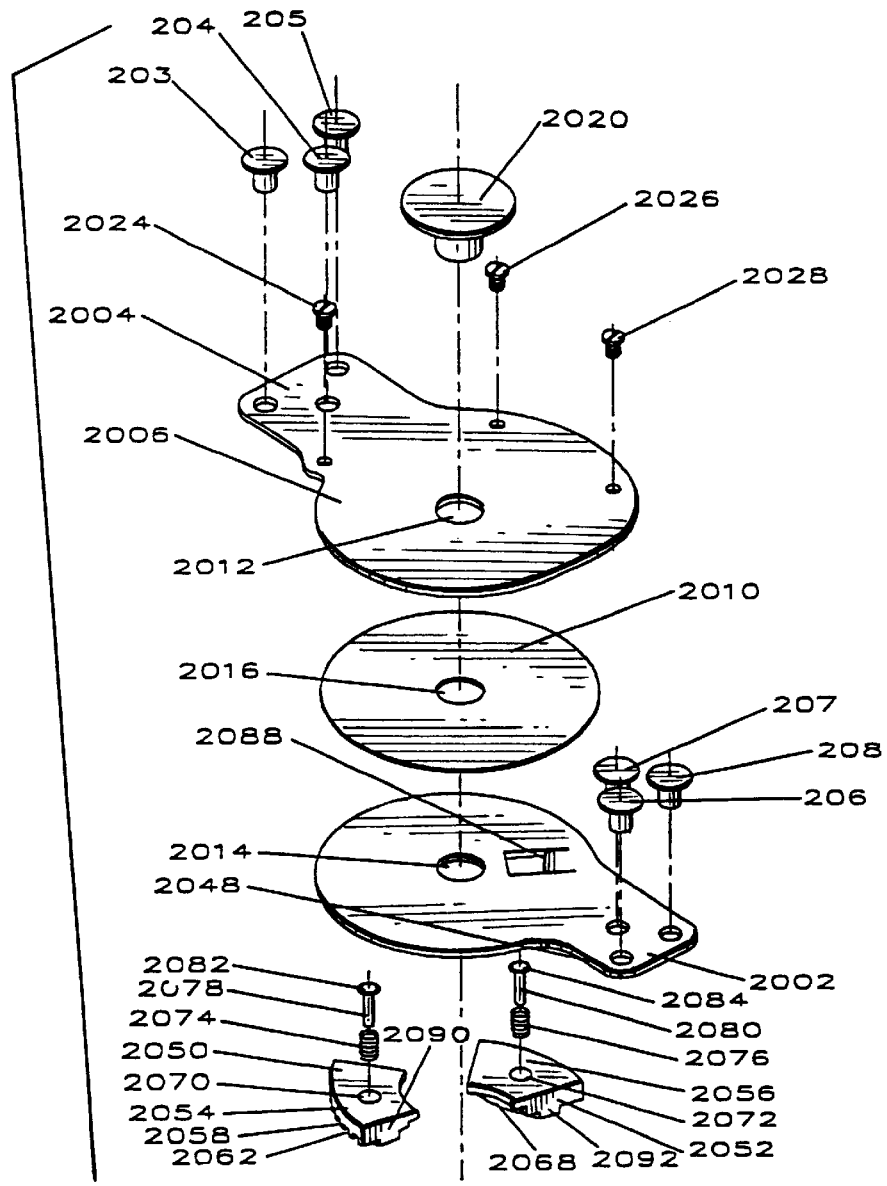
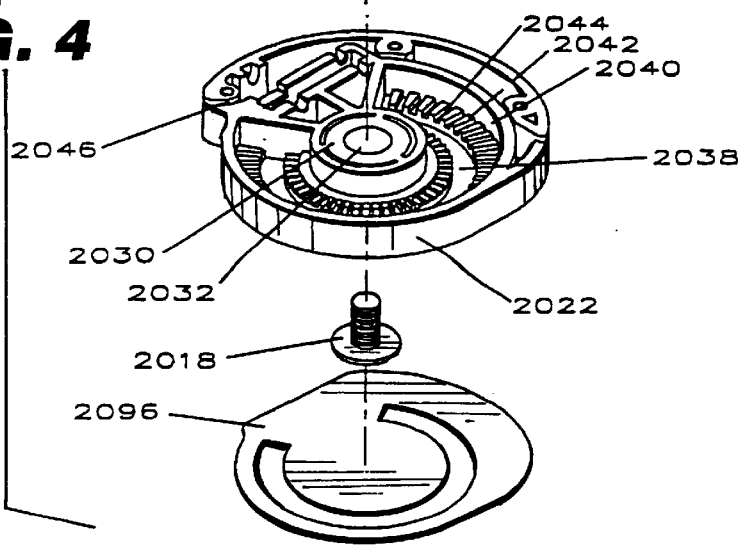
FIG. 4

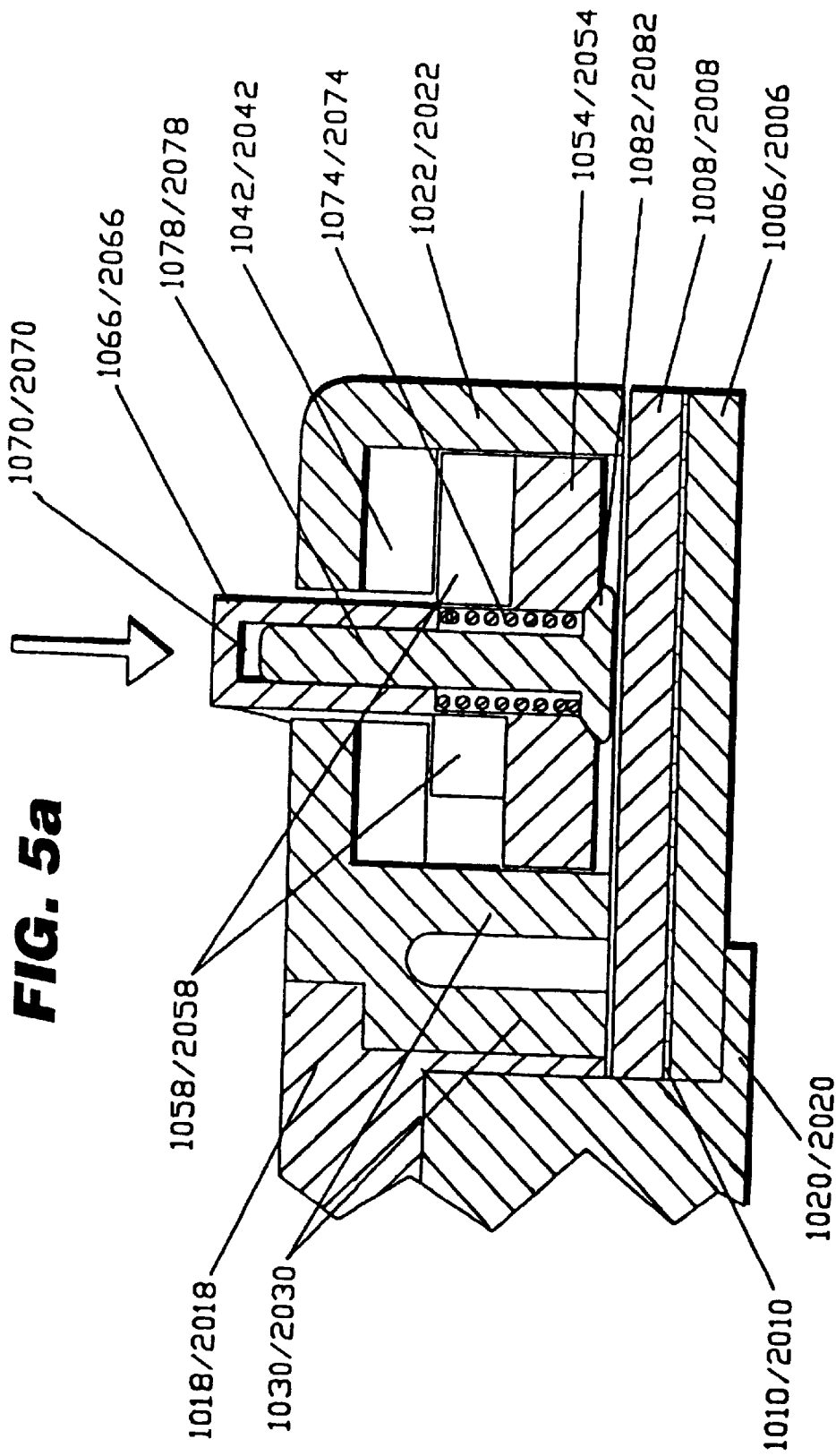

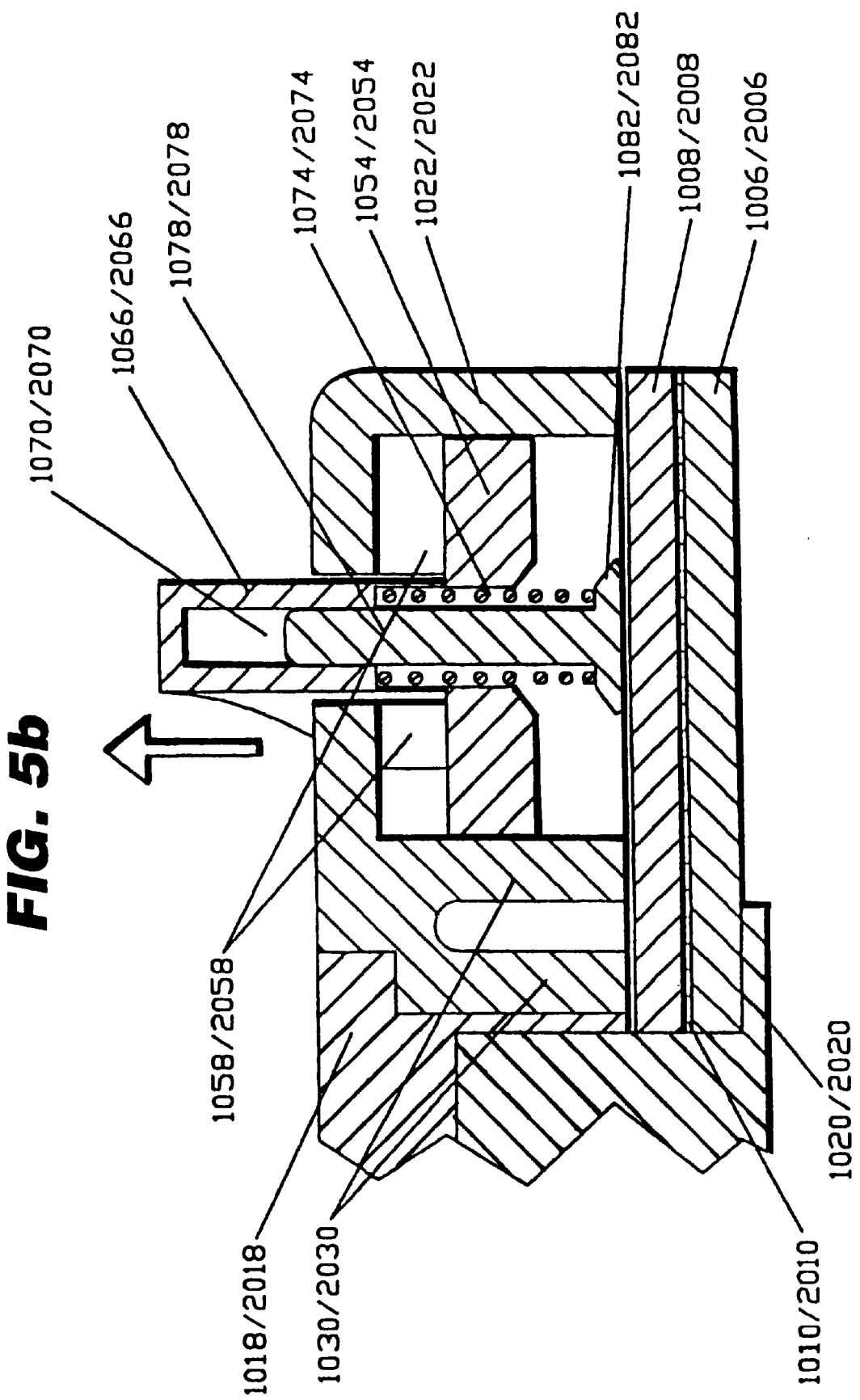

"HINGE WITH MOVEMENT LIMITATION"

BACKGROUND OF THE INVENTION

This invention relates to a hinge with movement limitation for use in orthoses, orthopaedic splints and braces employed at the knee.

Mechanically, the knee is a modified, crossed, four bar linkage comprising the rigid elements femur, tibia and the anterior and the posterior cruciate ligaments. Its axis of rotation moves backwards or posteriorly as the knee is flexed from the fully extended position. The locus or track of the axis of knee rotation is called the "Instant Centre Pathway" which exactly defines the moving path of the centre of knee rotation at any given instant.

In a first, very widely used type, there are two hinge arms each having its own pivot and also each having a set of gear teeth about the periphery of that part which extends between the pivots. The arms are so sized and arranged that the gear teeth mesh between the pivot points, thereby integrating the arm movements. Thus if one arm moves, the other must move as well. This type is generally referred to by those skilled in the art as the geared bi-axial, geared duocentric or geared polycentric type. The latter term is perhaps the most widely recognised. This type of hinge is not at all physiological in the way it moves and its mechanical action is quite unlike that of the human knee. Consequently such a hinge cannot accommodate or track the complex motion of the knee properly.

Another type of hinge design used in orthopaedic splints and braces employed at the knee has two hinge arms, each having its own pivot but in this design there are no gear teeth. Thus, in this type, the arm movements are not integrated and each arm can always move independently without affecting the other. This type of hinge is generally referred to by those skilled in the art as the true bi-axial, true bi-pivotal or simply just bi-pivotal type. It continues to grow in popularity with the realization that such a construction is superior to the others in providing the freedom necessary to accommodate the complex and changing locus of the axis of the knee throughout the entire flexion/extension cycle.

However, a third type, only slightly less popular than the geared polycentric type, has two hinge arms which are joined at and flex about a single pivot. This type is generally referred to by those skilled in the art as the uni-axial, uni-pivotal or monocentric type. Like the geared polycentric hinge, this type is not physiological but because it can be made simply and cheaply, basic designs have frequently found favour in braces and orthoses used in the early phases of treatment and rehabilitation following injury to or surgery on the knee, such as rupture and repair of the anterior cruciate ligament. Most users and manufacturers are aware that uniaxial hinges offer little in the way of physiological tracking or accommodation of natural knee motion. However, the argument made by both groups in favour of using uniaxial hinge usually relates to cost and also propounds that in the acute situations, where most use of this type occurs, ranges of motion are small and activity levels are low.

The origin of single pivot hinges in general is lost in the mists of time but it is found in pre-historic flails used for grain and in early jewellery. The uniaxial hinge has been used in a basic form since the earliest days of the orthotic profession and this probably emerged from its widespread earlier use by makers of military armour.

In 1855, H. H. Smith writing in the American Journal of Medical Science described a true splint but which he called an "artificial limb" which featured a uniaxial hinge at the knee. It does not appear to have had any means for controlling flexion or extension. In 1866, U.S. Pat. No. 58,403 to R. J. P. Goodwin, described a splint primarily for fractures which had a uniaxial hinge and a slot and screw arrangement for compressively locking the arms of the splint in a selected position in what is effectively a continuously variable manner.

In 1889, U.S. Pat. No. 401,933 to W. H. De Camp, described a fracture apparatus for surgeons' splints which had a uniaxial hinge with a body in the form of a disk segment, attached to one hinge arm and provided with a series of openings to receive a pin mounted on an auxiliary spring arm carried on the same pivot rivet as the arms. This arrangement provided flexion stops or discontinuous extension stops but not both at the same time. Free motion of the hinge could be provided by moving the auxiliary spring arm beyond the extent of the disk.

A somewhat similar but simplified arrangement is described in U.S. Pat. Nos. 4,481,941 and 4,531,515 to Rolfes. In these devices a pair of substantially circular hinge plates are at the end of a first hinge arm and a second hinge arm is disposed between them. Both plates have a series of aligned holes but those in the rearmost plate may be threaded. Pins constituting discontinuously variable stop means are passed non-threadedly through the front plate and engage optionally threadedly with the rear plate.

In U.S. Pat. No. 4,738,252, to Friddle et al, a uniaxial joint is described with means for controlling flexion and extension stop positions defined by the length of an arcuate slot acting against a stop pin. In addition, means are provided, in the form of mutually engaging serrated members, for repositioning the arcuate slot. No means for selectively altering the stop position within the arcuate slot, are disclosed.

U.S. Pat. No. 4,982,732 to Morris discloses a uniaxial knee brace having a slotted circular hinge member, 16 discrete radial stops for extension and a further 16 discrete stops for flexion, each stop being provided with its own leaf spring. The stops extend through slots in a cover which bear some resemblance to those of De Camp op cit. Both sets of stops may be individually and selectively moved from a disengaged or parked position in a circular hinge member to an engaged position where they contact abutment stops formed in a circular cam member, thus limiting flexion and extension in a discontinuous manner.

U.S. Pat. No. 5,000,169, to Swicegood et al, employs a serrated indexing ring plate which the authors call a rounded serrated track. Movable, separate stop carriers for discontinuous limitation of flexion and extension are mounted in arcuate slots within the plate. Stops are in the form of pins which engage both a recess in the serrated track and a hinge base plate.

SUMMARY OF THE INVENTION

According to the present invention there is provided a hinge for use in an orthopaedic brace or orthosis comprising: a first hinge member and a second hinge member, the two hinge members being generally planar in parallel planes and relatively rotatable about an axis perpendicular to the planes of the hinge members, the first hinge member having at least one limiting means which is selectively lockable in variable incremental positions by means of engaging teeth, the second hinge member having a projection which prevents relative movement of the hinge members in a given direction once the projection contacts the limiting means.

Preferably, the first member has two limiting means variably disposed on either side of the projection.

Preferably, the limiting means is biased towards the first hinge member such that a force is required to vary the incremental position of the limiting means in relation to the first hinge member.

Preferably, the first hinge member has a slot and the limiting means is in the form of a projection slot into the slot. The slot may be arcuate and centered on the axis.

The first and second hinge members are preferably generally circular plates with a central perpendicular axis about which the plates are rotatable.

The first hinge member may have front and back portions which generally surround the second hinge member.

The single axis rotatable hinge is particularly for use in an orthosis or orthopaedic brace for selectably controlling the range of motion at a joint, particularly the knee joint, in a discontinuous equi-incremental.

A uniaxial orthopaedic hinge includes a locking plate and a back plate, each having an extension forming a hinge stub arm and both being generally substantially circular. The diameter of the locking plate is somewhat less than that of the back plate.

The locking plate and back plate, which are preferably formed in metals by pressing, are disposed either side of a circular plastic shim in a co-planar and concentric manner and these elements are mutually adapted, by the provision of a suitably sized central hole, to receive pivotal and securing means in the form of a pivot bolt and nut assembly.

A substantially circular recessed housing member, made conveniently in strong plastics by moulding, is so sized that it fits over the circular end of the back plate and is secured to part of the periphery thereof by suitable fixing means and is also adapted, by the provision of a central boss and through hole, to receive the pivot bolt and nut assembly.

The assembly, thus formed, deploys the back-plate with the locking plate secured to and sandwiched between it and the circular recessed housing member, the whole forming the hinge body. The plastic shim provides means for improving the smooth running characteristics of the hinge.

The circular recessed housing member is further provided with a concentric and arcuate through-slot, disposed inwardly from the periphery. Disposed on either side of the inner surface of the arcuate slot and interrupted by it are equally spaced parallel sided radial teeth.

Adjustable hinge stop and locking means are in the form of two substantially similar quadrant-shaped elements, one to control extension, the other to control flexion. Each quadrant is provided with releasing means in the form of a pusher extending centrally from and disposed at 90° to a base and which in the assembled condition, locates in and extends through the arcuate slot in the circular recessed housing member. Releasably securable stop means are in the form equally spaced parallel sided radial toothed locking faces disposed on the base portion, on the same surface as and on either side of, the pusher. The radial teeth of the locking faces are adapted so as to engage, fully and intimately, with those provided on the inner aspect of the circular recessed housing. The end faces of the quadrants constitute abutment stop means.

The quadrant shaped elements are each provided with a circular recess disposed centrally within the base. Each recess provides housing means for a compression spring fitted with a round headed pin, which, in the assembled condition, acts against the locking plate to sustain the engagement between the radial teeth of the quadrants and the spaces between the radial teeth on the inner aspect of the circular recessed housing.

A quadrant may be disengaged from the circular recessed housing by depressing the pusher to overcome the action of the compression spring. The quadrant may then be moved along the arcuate through-slot to a new stop position. Quite small increments may be achieved and incremental markings may advantageously be displayed on the outer face of the circular recessed housing member.

The locking plate is provided with a small upstanding flange which in the assembled condition extends centrally into the arcuate slot, the edges providing first and second abutment stop means each adapted to co-operate with one end face of each quadrant. By these means the hinge may be allowed any desired range of angular motion which is a multiple of the small angular increments of the radial space angle. In addition, the dimensions of the quadrants the spacing of the radial teeth and the flange are so arranged that the hinge may be locked in a selected position.

The instant invention employs few parts and is simple and easy to construct and is economical to supply. Incremental angles are generally smaller than in prior art incremental range of motion hinges. Adjustments to the extension and flexion quadrants of the instant hinge may be made rapidly and easily and no special tools are required.

It is a first important object of the present invention to provide a uniaxial, orthopaedic, range of motion hinge which provides for adjustment of extension and flexion by releasable mutual engagement between radial teeth disposed on the inner surface of a hinge body housing about an arcuate through-slot and radial spaces provided on quadrant extension and flexion stops moveable between selectable incremental stop positions within the arcuate slot.

It is yet a further object of the present invention to provide a uniaxial, orthopaedic, range of motion hinge which allows more rapid and positive incremental adjustment of extension and flexion stops than with prior art hinges.

It is yet a further object of the present invention to provide a uniaxial orthopaedic range of motion hinge which meets the foregoing objects whilst using only a small number of parts.

BRIEF DESCRIPTION OF THE DRAWINGS

An embodiment of a hinge in accordance with the present invention is now described with reference to the accompanying drawings in which:

FIG. 4 is an exploded perspective view of the hinge of FIG. 2, showing the principal components.

FIGS. 5a and 5b are sections of the toothed quadrant range of motion flexion and extension control mechanism of FIG. 2. showing "stop" and "travel" positions.

DETAILED DESCRIPTION OF THE INVENTION

In order that the present invention may be more readily understood, general reference will now will be made to FIGS. 1 to 5b.

Figure 1:
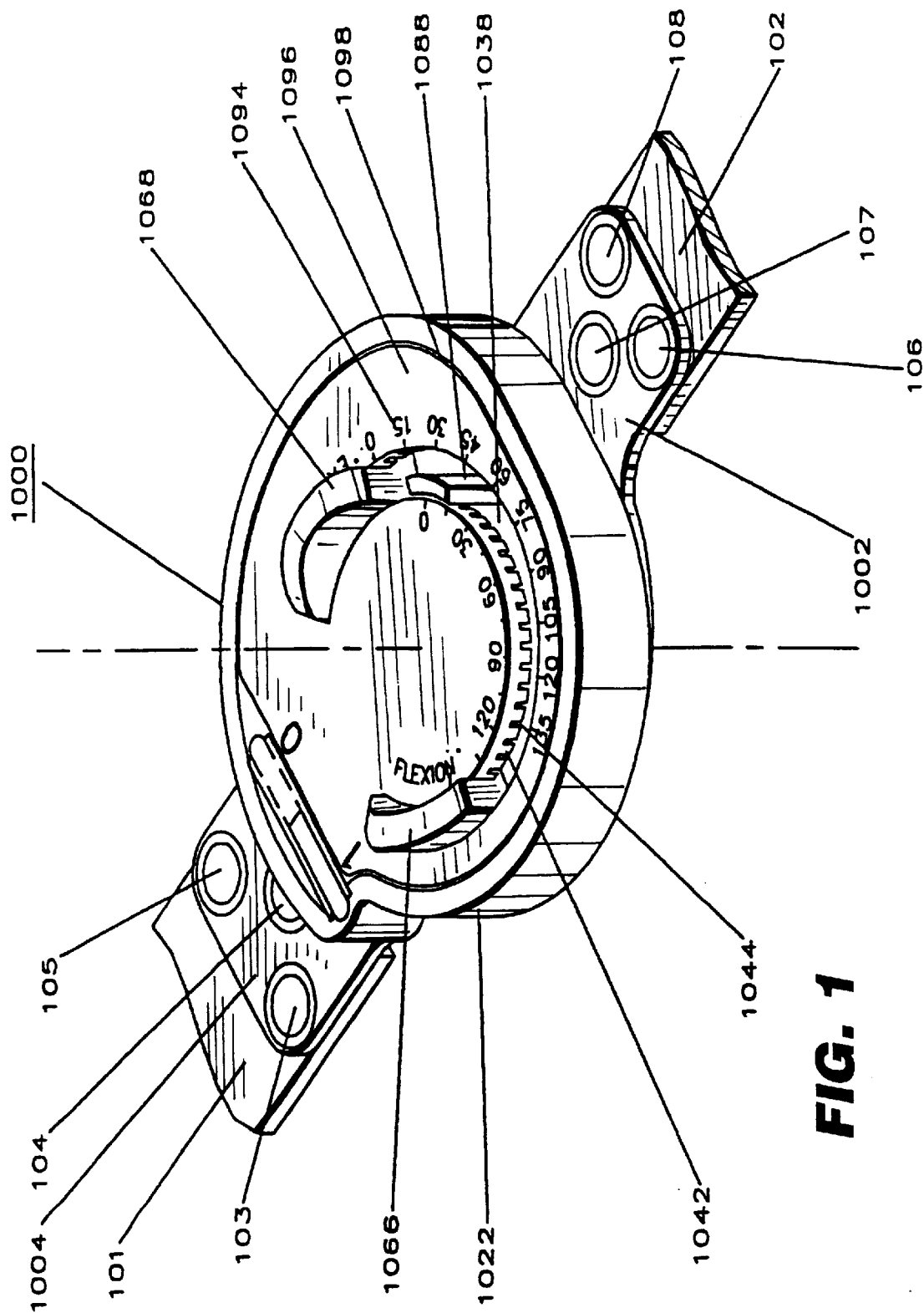
FIG. 1 is a diagrammatic perspective front view of a left hand hinge according to the present invention.
Figure 2:
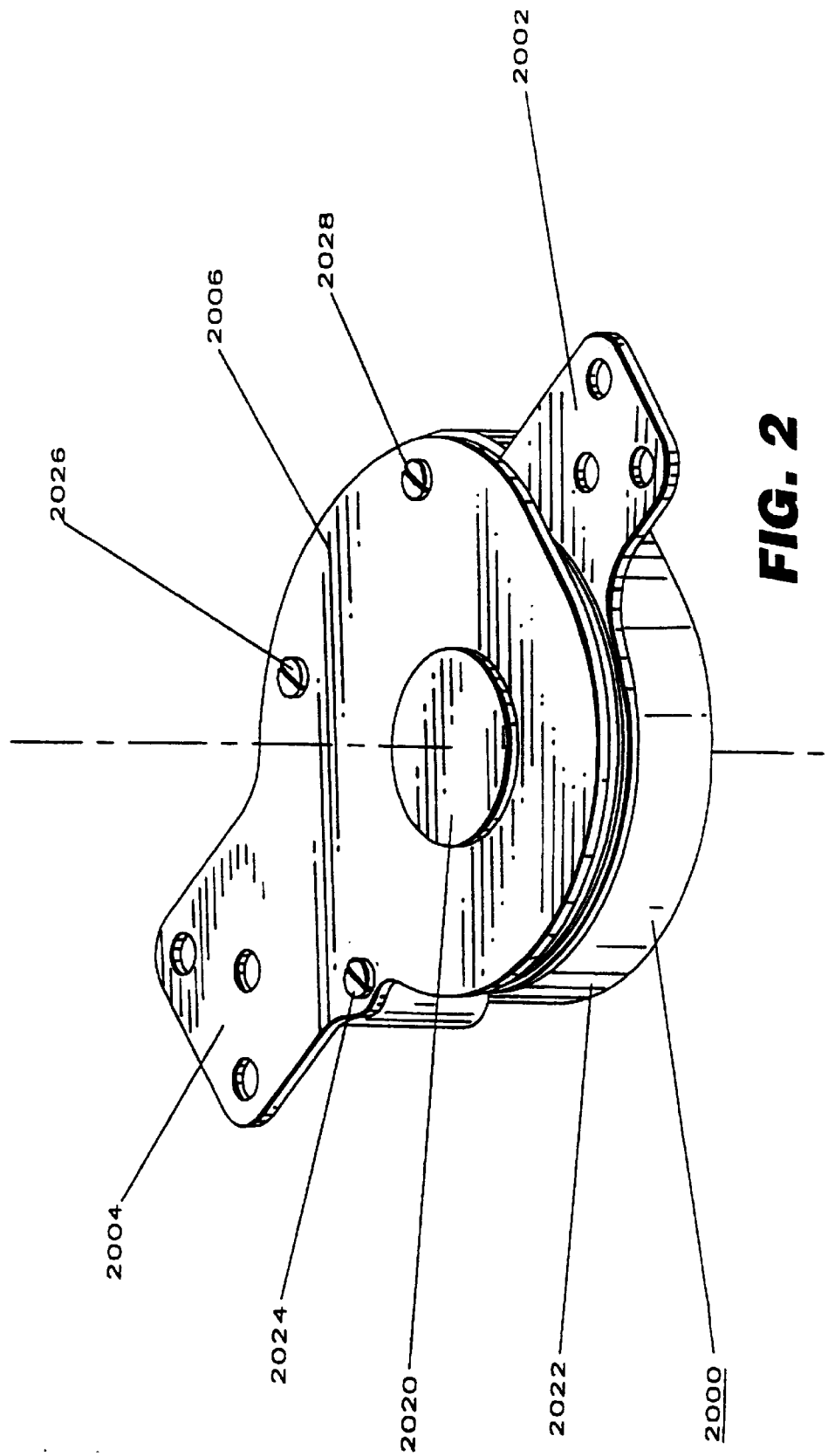
FIG. 2 is a diagrammatic perspective back view of a right hand hinge according to the present invention.

Referring first to FIG. 1, there is shown a diagrammatic, perspective, front view of a left hand single axis rotatable hinge 1000, according to the present invention, for use in an orthosis or orthopaedic brace, for selectably controlling the range of motion at a joint in a human limb. FIG. 2 shows a diagrammatic perspective back view of a right hand hinge 2000, the right hand hinge being substantially a mirror image of left hand hinge 1000. Brace arms 101 and 102 are secured to a left locking plate stub arm 1002 and left back plate stub arm 1004 by rivet means 103 to 108. This arrangement is preferred because it allows aluminium, which has the advantage of being light, to be used for generic brace arms which are generally quite large. In contradistinction back plates 1006 and 2006 and locking plates 1008 and 2008, according to the present invention are relatively small but are preferably made in stainless steel for strength and longevity.

Figure 3:
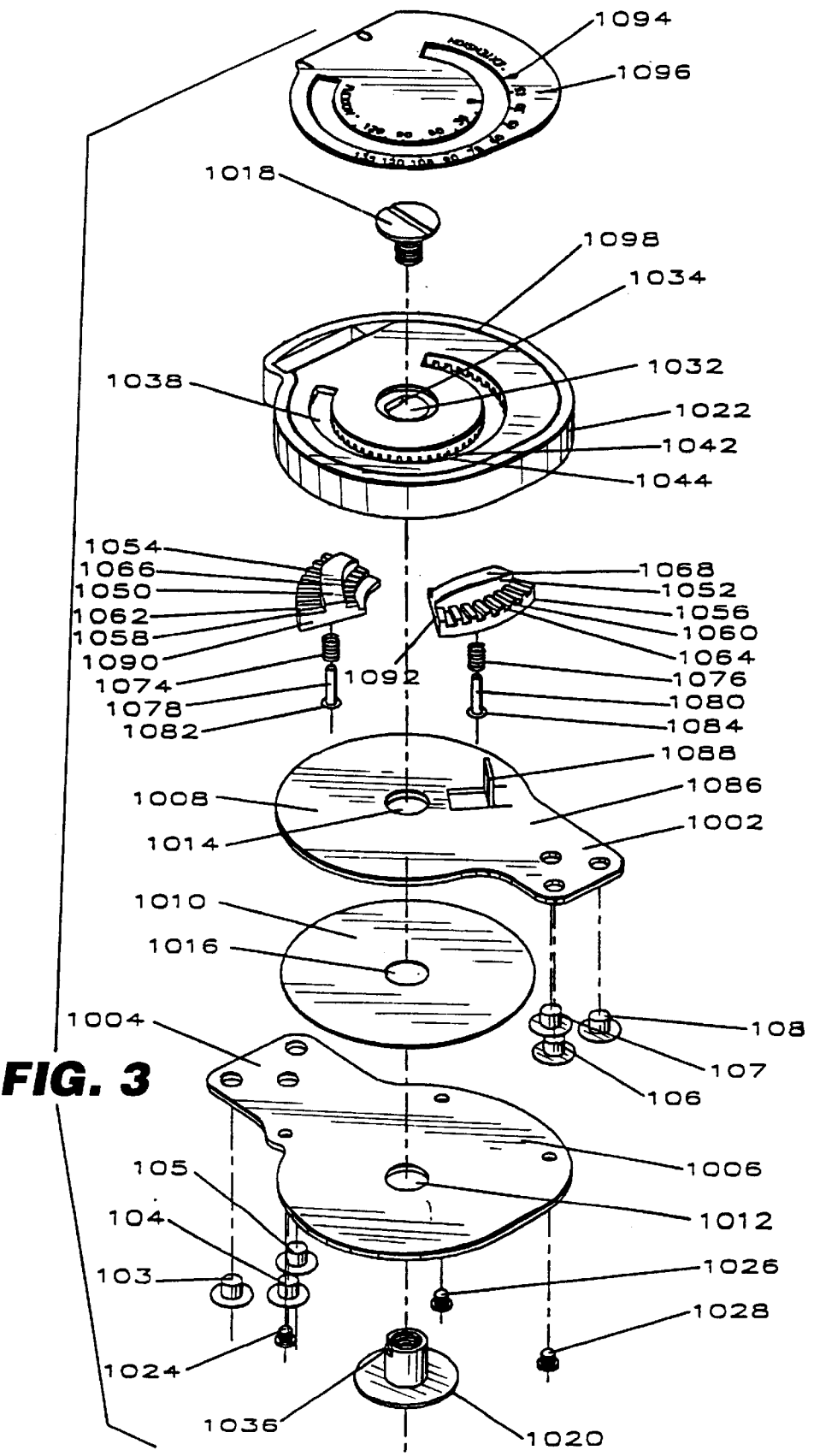
FIG. 3 is an exploded perspective view of the hinge of FIG. 1, showing the principal components.

As may best be seen with reference to FIGS. 3 and 4, back plates 1006 and 2006 and locking plates 1008 and 2008 are substantially circular, the diameters of the locking plates being slightly less than the principal diameter of the back plates which are extended and have a secondary, larger diameter. These elements are preferably manufactured commercially by pressing. Back plates 1006 and 2006 and locking plates 1008 and 2008 are spaced apart in a co-planar and concentric manner by circular plastic shims 1010 and 2010, which ensure smooth operation of the assembled hinges 1000 and 2000. Elements 1006; 2006, 1008; 2008 and 1010; 2010 are mutually adapted, by the provision of a central circular holes 1012; 2012, 1014; 2014 and 1016; 2016, respectively, of equal diameter, to receive slidingly, pivotal and securing means in the form of pivot bolts 1018; 2018 and blind flat headed nuts 1020; 2020.

Hinges 1000 and 2000 are each provided with a substantially circular recessed housing 1022 and 2022 respectively which is preferably moulded in high definition thermoplastics such as nylon 6 reinforced with 50% glass fibre for toughness. Alternatively, these components may be cast in a suitable aluminium alloy. The housings 1022 and 2022 are so sized that they fit over those parts of the peripheries of back plates 1006; 2006 which are not involved in flexion and extension motion and are each secured thereto by screw fixing means 1024, 1026, 1028 and 2024, 2026 and 2028. The housings 1022 and 2022 are each also adapted, by the provision of a central boss 1030; 2030, respectively having a through hole 1032; 2032, to receive pivot bolt 1018; 2018 and nut 1020; 2020.

Bosses 1030 and 2030 are each adapted by the provision of a flat 1034; 2034 to receive slidingly and non-rotatably, corresponding adaptations of part of each of the distal shanks of blind flat headed nuts 1020; 2020 in the form of flats 1036; 2036.

Circular recessed housings 1022 and 2022 are each further provided with a concentric and arcuate through-slot, 1038; 2038, disposed inwardly from the periphery and extending over rather more than 270°. The recessed inner surface aspect 2040, of the circular recessed housing member 2022, may be seen in FIG. 4, to be provided with a series of parallel sided radial teeth indicated by way of example in perspective underplan view at 2042 and seen somewhat less clearly in edge view in FIG. 3 at 1042. Tooth series 1042 and 2042, are each separated and spaced apart by a series of equi-angular radial slots, indicated by way of example at 1044 and 2044. Reference to FIGS. 3 and 4 will indicate that tooth series 1042; 2042 and slot series 1044; 2044 are disposed along either side of and are interrupted by arcuate through-slots 1038; 2038.

Absolute hyperextension stop means are provided within moulded circular recessed housings 1022 and 2022 as indi-
cated in FIG. 4 at 2046. This raised edge constitutes an abutment stop for edge 2048 of locking plate stub arm 2002.

Adjustable flexion and extension stop means and locking means for each hinge are in the form of a pair of mirror image but otherwise substantially similar quadrant-shaped elements 1050; 1052 and 2050; 2052. These elements are preferably moulded in the same material as that used for circular recessed housings 1022 and 2022. Releasably securable stop means are disposed on base portions 1054; 1056 and 2054; 2056 in the form of a series of parallel sided radial teeth indicated by way of example in perspective overplan view at 1058 and 1060, in FIG. 3. Tooth series 1058; 1060 and 2058; 2060 are each separated and spaced apart by a series of equi-angular radial slots, indicated by way of example at 1062 and 1064. Tooth series 1058; 1060 and 2058; 2060 and radial slot series 1062; 1064 and 2062; 2064 are each adapted to mesh intimately, lockably and releasably with radial slot series 1044; 2044 and tooth series 1042; 2042, respectively, of circular recessed housings 1022 and 2022.

Quadrants 1050; 1052 and 2050; 2052 are each provided with releasing means in the form of arcuate, convex-headed, pushers 1066; 1068 and 2066; 2068 extending at 90° from base portions 1054; 1056 and 2054; 2056, such that in the assembled condition, these elements locate in and extend through arcuate slots 1038; 2038 in circular recessed housings 1022 and 2022.

Engagement biasing means are provided in the bases 1054; 1056 and 2054; 2056, of each of quadrants which are moulded or cast with a central blind circular hole, seen in FIG. 4 at 2070 and 2072, adapted to receive biasing compression springs 1074; 1076 and 2074; 2076, respectively and within them, pins 1078; 1080 and 2078; 2080. The blind holes, spring and pins are so sized that, in the assembled condition, rounded heads 1082; 1084 and 2084; 2086 of pins 1078; 1080 and 2078; 2080, are compressed against the faces of the locking plates. This arrangement thereby sustains the engagement between the radial slot series 1044; 2044 and tooth series 1042; 2042 of the circular recessed housings 1022 and 2022 and radial teeth series 1058; 1060 and 2058; 2060 of parallel sided radial teeth and radial slot series 1062; 1064 and 2062; 2064, of quadrants 1050; 1052 and 2050; 2052. This is best seen with reference to face 1086, of locking plate 1008, in FIG. 3.

Locking plates 1008 and 2008 are further adapted to co-operate with quadrants by the provision of limiting abutment stop means in the form of a parallel sided tongue or flange 1088; 2088, formed preferably by a three-sided pierce and broach through the back face during manufacture. This element is formed in such a position that, in the assembled condition, it always lies centrally under arcuate though-slots 1038; 2038. Corresponding abutment stop means are provided on those quadrant end faces 1090; 1092 and 2090; 2092, which enclose the flexion angle.

By these novel means hinges 1000; 2000, of the present invention may be set to provide any desired limited range of angular motion which is a multiple of the angular increments of the spacing of the teeth and slots in the quadrants and the circular recessed housings. In addition, flanges 1088; 2088, are so sized in relation to the size of the quadrants and spacing of the teeth and slots provided thereon that the hinges may be locked in large number of selected positions.

A structurally equivalent, through somewhat less preferable alternative to the flange may be provided separately, for instance in the form of a small casting, subsequently attached with suitable fixing means, such as a screw, in the corresponding position on the locking plate. This solution is more costly in terms both of materials and labour.

As may be seen with particular reference to FIGS. 5a and 5b, to set new stop positions and thus to change the range of motion for hinges 1000; 2000, the pusher of each quadrant is depressed to overcome the action of the compression spring. The radially toothed and slotted locking faces of the quadrants thus become disengaged from the radial teeth and slotted faces on the inner aspect of the circular recessed housings. So long as the pusher is depressed, the quadrant is in the "travel" position and may be moved along the arcuate through-slot to a newly selected stop position. In this preferred embodiment it has been possible to achieve discrete increments of 7.5°. In order to ensure that the same flexion and extension positions may be set on each of a pair of hinges mounted medially and laterally with respect to a joint, it is important to provide clear incremental markings on the outer face, of the recessed housings 1022; 2022. These are indicated at 1094 in FIG. 3. Incremental markings are preferably presented using accurately printed and registered applique labels 1096; 2096 rather than embossing or debossing the moulding itself. This is because more contrasting and precise markings may be provided with the label method. Registration is achieved by incorporating a suitable bezel into the moulding, indicated at 1098, in FIG. 3.

In an alternative embodiment, a hinge is provided in which the flexion is unlimited. In this embodiment, a single variable quadrant 1052; 2052 is provided for varying the degree of extension. A fixed stop is provided for the flexion.

The limiting means are described herein as quadrants although other shapes may be used. A plurality of teeth 1042; 2042 are provided on each limiting means in order to distribute the force exerted on the limiting means when the limiting abutment stop means 1088; 2088 contacts it to prevent shearing of the teeth 1042; 2042.

In marked contradistinction to prior art range of motion control mechanisms employed in uniaxial hinges, the present invention provides for incremental adjustments which are finer and extend over more than the physiological range by the provision of a flexion control quadrant and an extension control quadrant having radial teeth separated by radial spaces and adapted to releasably engage with corresponding structures in a suitable recessed housing.

The instant invention employs only a small number of parts and is, therefore, generally simpler and easier to construct and more economical to supply than prior art range of motion hinges. Additionally, the instant hinge offers incremental adjustment at smaller incremental angles than are generally available with prior art incremental range of motion hinges. Furthermore, adjustments to the extension and flexion stops of the instant hinge may be made more rapidly and easily than with previous hinges and no special tools are required.

The preferred embodiment of the present invention immediately hereinbefore described is given by way of example and it will be clear to those skilled in the art that numerous other variations may be derived from this disclosure without departing from the scope, intent and spirit of the novelty thereof.

I claim:

1. A hinge for use in an orthopaedic brace of orthosis comprising:

a first hinge member and a second hinge member, the two hinge members being generally circular plates and being planar in parallel planes and relatively rotatable about a central axis perpendicular to the planes of the hinge members, the first hinge member having an arcuate slot extending at least 180 degrees and centered on the axis of the hinge and at least one limiting means which is selectively lockable in variable incremental positions by means of a plurality of engaging teeth, said limiting means including a pusher which is biased through said slot and which can be manually depressed parallel to the hinge axis of rotation to disengage the engaging teeth to allow the limiting means to be repositioned, the second hinge member having a projection which prevents relative movement of the hinge members in a given direction once the projection contacts the limiting means.

2. A hinge as claimed in claim 1, wherein the first hinge member has two limiting means variably disposed on either side of the projection.

3. A hinge as claimed in claim 1, wherein the limiting means is spring biased toward the first hinge member such that a manually applied force is required to vary the incremental position of the limiting means in relation to the first hinge member.

4. A hinge as claimed in claim 1, wherein the first hinge member has front and back portions which generally surround the second hinge member.

\* \* \* \* \*